United States Patent [19]

Suzuki et al.

[11] 3,962,267

[45] June 8, 1976

[54] DENTAL CEMENT COMPOSITION

[75] Inventors: Narishige Suzuki, Kyoto; Yoshihiro Morino, Otsu; Yoshitaka Hashiguchi, Amagasaki; Tunehiro Segawa, Sakai, all of Japan

[73] Assignees: Shofu Dental Corporaton, Kyoto; Teikoku Chemical Industry Co., Ltd., Osaka, both of Japan

[22] Filed: July 11, 1974

[21] Appl. No.: 487,486

[30] Foreign Application Priority Data

Apr. 16, 1974 Japan.............................. 49-43179

[52] U.S. Cl............................... 260/29.6 TA; 32/15; 260/29.6 H; 260/29.6 M; 260/42.29; 260/42.43; 260/42.52; 260/998.11

[51] Int. Cl.².......................................... C08K 3/22

[58] Field of Search .... 260/42.29, 998.11, 29.6 TA, 260/29.6 M, 29.6 H

[56] References Cited

UNITED STATES PATENTS

| | | | |
|---|---|---|---|
| 3,655,605 | 4/1972 | Smith et al............................ | 106/35 |
| 3,837,865 | 9/1974 | Pellico............................ | 260/998.11 |
| 3,882,080 | 5/1975 | Schmitt et al.................. | 260/998.11 |

*Primary Examiner*—James H. Derrington
*Attorney, Agent, or Firm*—Jones, Tullar & Cooper

[57] ABSTRACT

The dental cement composition comprises an aqueous resin composition prepared by the copolymerization of 3-butene-1,2,3-tricarboxylic acid and an $\alpha,\beta$-olefinic unsaturated monocarboxylic acid and, when desired, an additional polymerizable monomer as well as a metal oxide. The dental cement composition possesses compressive strength.

8 Claims, No Drawings

DENTAL CEMENT COMPOSITION

The present invention relates to a dental cement composition and, more particularly, to a dental cement composition possessing an excellent compressive strength.

Dental cements which are conventionally used are classified into the following groups: cements for cementation of inlays, crowns, bridges or the like, cements for filling a cavity in a tooth, lining cements for filling a cavity with other materials, and so forth. For these purposes, there are used zinc phosphate cements, polycarboxylate cements or the like which are prepared, for example, in combination of a polymer of a phosphate or an unsaturated carboxylic acid, with a metal oxide. These cements have been practically applied in large amounts over a long period of time; however, they have still some properties to be improved. For example, zinc phosphate cements will cause harm to tooth pulp because of the use of the acids. The polycarboxylate cements usually do not give a satisfactory compressive strength.

As the result of extensive studies, it has been found that the use of a resin composition containing 3-butene-1,2,3-tricarboxylic acid as a monomer constituent, together with a metal oxide can provide a dental cement composition with an excellent compressive strength.

The object of the present invention is to provide a dental cement composition comprising a resin composition prepared by the copolymerization of 3-butene-1,2,3-tricarboxylic acid and an $\alpha,\beta$-olefinic unsaturated monocarboxylic acid and, when desired, an additional polymerizable monomer, as well as a metal oxide. Other objects, features and advantages of the present invention will become apparent during the course of the following description and the claims.

The 3-butene-1,2,3-tricarboxylic acid of the present invention may be prepared, for example, by processes described in Japanese Patent Publication Nos. 19,845/1969 and 13,690/1969, e.g., by reacting an acrylic acid ester with a fumaric acid diester, under a nitrogen atmosphere, in an organic solvent, in the presence of a catalyst such as tricyclohexylphosphine, at an elevated temperature, while being stirred, removing the solvent and the materials unreacted from the reaction mixture, distilling the reaction mixture, and hydrolyzing the resulting 3-butene-1,2,3-tricarboxylic acid triester.

Monomers containing a carboxyl group which are conventionally used for polycarboxylate cements include, for example, acrylic acid, methacrylic acid, glutaconic acid, aconic acid, citraconic acid, mesaconic acid, itaconic acid, fumaric acid, maleic acid and tiglic acid. Where a multi-basic acid is used as a constituent, it is generally considered difficult to effect the polymerization, causing a problem with the formation of a resin composition. The resulting resin composition is generally unable to give a satisfactory effect required for a dental cement composition because of the effects which seem to be derived from an activity attributable to its carboxyl groups. In fact, a polycarboxylate cement containing a resin composition prepared from a relatively large amount of a multi-basic acid as a constituent is previously unknown. The present invention nevertheless renders it feasible to use such a resin composition containing a multi-basic acid or 3-butene-1,2,3-tricarboxylic acid as a constituent. This effect can be said to be unexpected from ordinary knowledge of one skilled in the art.

The $\alpha,\beta$-olefinic unsaturated monocarboxylic acids of the present invention include, for example, acrylic acid and methacrylic acid. They can be used alone or in combination. The other type of the polymerizable monomers which may optionally be used includes, for example, esters of the acrylic acid and methacrylic acid, in particular lower alkyl esters thereof, unsaturated carboxylic acids such as, for example, itaconic acid, maleic acid, fumaric acid and aconic acid and esters thereof, particularly lower alkyl esters thereof, 3-butene-1,2,3-tricarboxylic acid alkyl esters, preferably lower alkyl esters thereof, vinyl acetate and styrene. These monomers may vary in their kind and amount in which they are used, depending upon the viscosity of the resin composition and the compatibility with a metal oxide and the dispersibility thereof. Where the unsaturated carboxylic acid alkyl ester is employed as the polymerizable monomer, the resulting resin composition may be used for the dental cement composition of the present invention by hydrolyzing the ester group thereof with an alkali or an acid into the free carboxyl group.

In preparing the resin composition, the copolymerization of the polymerizable monomers may be effected, for example, by stirring 3-butene-1,2,3-tricarboxylic acid and acrylic acid in a mixed solvent of water and an alcohol under an inert gas atmosphere, for example, nitrogen gas, in the presence of a polymerization catalyst such as, for example, sodium persulfate or ammonium persulfate for about 2 to 7 hours at a temperature of about 60° to 70° C. After the polymerization reaction is completed, the resin composition may be obtained by subjecting the reaction mixture simultaneously to the elimination of the alcohol and condensation while the reaction mixture is kept warm. The resin composition of the present invention may preferably contain more than about 40 percent of solid materials. The resin composition containing the solid materials in concentrations less than about 40 percent shows a tendency to a decrease in the compressive strength. When the $\alpha,\beta$-olefinic unsaturated monocarboxylic acid is employed in a relatively large amount, for example, in an amount of more than 65 percent, the addition thereof in portions will be preferably carried out. The molecular weight of the polymer is usually within a range from about 5,000 to 250,000. The preferred viscosity of the aqueous copolymer solution is from about 100 to 8,000 cps. The higher the viscosity, the higher the compressive strength would be.

The 3-butene-1,2,3-tricarboxylic acid is usually used in a ratio of about 5 to 60 parts by weight thereof to 100 parts by weight of the total amount of the monomers. The amount of the tricarboxylic acid is preferably about 5 to 45 parts by weight based upon 100 parts by weight of the total amount of the monomers when particularly a high compressive strength is required. If such a high strength is not required, about 45 to 60 parts by weight of the tricarboxylic acid will be employed. The use of amounts larger than 60 parts by weight thereof will make it hard to effectively produce the resin composition industrially because of the low reactivity of the tricarboxylic acid for polymerization.

The amount of the $\alpha,\beta$-olefinic unsaturated monocarboxylic acid may be from about 40 to 95 parts by weight with respect to 100 parts by weight of the total amount of the monomers. The amount of the other class of the polymerizable monomer which may be added when desired will be from about 0 to 15 parts by weight with respect to 100 parts by weight of the total amount of the monomers used.

The metal oxide to be employed as a constituent includes those generally used for this purpose such as, for example, the oxides of zinc, magnesium, silicon, bismuth, barium, calcium, aluminum and titanium. They can be used alone or in combination. The metal oxide may be combined with the aqueous resin composition by treating it at about 800° to 1,300° C. in a conventional manner into powders having an appropriate particle size. The ratio of the aqueous copolymer solution to the metal oxide is from about 1 : 1 to 1 : 4 (copolymer : metal oxide), preferably from about 1 : 1 to 1 : 2.5.

Constituents which may be appropriately added may include, for example, halides, phosphates, sulfates, borates and silicates of a metal, preferably a monovalent metal thereof. Specific examples thereof are, for example, sodium chloride, sodium iodide and sodium sulfate. A solidification accelerator such as an organic acid; a solidification retarder, such as a phosphate; or an agent for improving the compressive strength such as citric acid or a phosphate; which may be conventionally used for these purposes, may be added in an appropriate amount.

The following examples illustrate the present invention without, however, limiting the same thereto. The units "part(s)" and "%" in the following examples mean a part or parts by weight and percent by weight, respectively.

EXAMPLE 1

To 150 parts of water and 50 parts of methanol were added 70 parts of acrylic acid and 30 parts of 3-butene-1,2,3-tricarboxylic acid. To this was added ammonium persulate in an amount of 2% with respect to the weight of the monomers. The mixture was then subjected to the polymerization reaction by warming it at a temperature of 60° to 70° C. and stirring it for 4 hours. After the completion of the polymerization reaction the reaction mixture was heated and concentrated to a resin having solid materials in a concentration of 44 percent. The viscosity of the resin was 2,500 cps. (measured by a BM-type viscometer manufactured by Tokyo Keiki K.K., Japan; at 25° C. and with 6 rotations).

95 parts of zinc oxide and 5 parts of magnesium oxide were calcined for 1 hour at 1,300° C. and ground into finely divided powders in such a manner that 50 percent of the powders had an average particle size of about 10 microns and formulated with the said resin composition. The resulting composition was tested according to A.D.A. Specification No. 8. The test results are shown as follows:

Table 1

| Standard consistency[1] | 1.5 g. |
| Time of setting | 6.5 minutes |
| Compressive strength[3] | 950.0 kg./cm.$^2$ |
| Film thickness | 22.0 $\mu$ |
| Tensile strength[2] | 60.0 kg./cm.$^2$ |
| Solubility & Disintegration | 0.03 % |

Notes
[1]The standard consistency was determined by sampling 1 gram of the resin solution and then measuring a quantity of powders therein according to said specification.
[2]The tensile strength was determined with a sample specimen 24 hours after the sample was prepared Table 1-continued in accordance with the Diametral method according to the following formula:

$$\text{Tensile strength, kg./cm.}^2 = \frac{2P}{\pi DL}$$

wherein P is a value observed (kg./cm.$^2$), D is a diameter of the sample and L is a length thereof.
[3]The compressive strength was determined by using a sample specimen 24 hours after it was prepared according to said specification.

EXAMPLES 2 TO 5

A resin composition was prepared by repeating the procedures of Example 1 except that the ratio of 3-butene-1,2,3-tricarboxylic acid to acrylic acid differed from that thereof in Example 1 and the latter was separately added in portions when the ratio of the former was not more than 40 percent. The resin composition was then mixed with a metal oxide and tested. The materials and results will be set forth in Table 2.

Table 2

| Examples | 2 | 3 | 4 | 5 |
|---|---|---|---|---|
| Acrylic acid, parts | 92 | 85 | 60 | 50 |
| 3-Butene-1,2,3-tricarboxylic acid, parts | 8 | 15 | 40 | 50 |
| Solids, % | 46 | 46 | 46 | 46 |
| Viscosity, cps. | 4,000 | 3,800 | 3,500 | 350 |
| Standard consistency, g. | 1.85 | 1.7 | 1.8 | 2.2 |
| Time of setting, min. | 6.5 | 7.0 | 6.5 | 7.0 |
| Compressive strength, kg./sq.cm. | 870 | 850 | 1,030 | 600 |
| Film thickness, $\mu$ | 20 | 19 | 21 | 19 |
| Tensile strength, kg./sq.cm. | 63 | 35 | 77 | 24 |
| Solubility & Disintegration, % | 0.03 | 0.03 | 0.03 | 0.03 |

EXAMPLES 6 AND 7

The resin of Example 4 and the oxides of metals (where 50 parts of alumina, 45 parts of zinc oxide, 3 parts of magnesium oxide and 2 parts of bismuth subnitrate were calcined at 1,300° C. and then ground into finely divided powders) in the amount of 50 parts and 30 parts in Examples 6 and 7, respectively, were mixed and treated and tested in the same manner as in Example 1.

The results will be shown in Table 3.

Table 3

| Examples | 6 | 7 |
|---|---|---|
| Standard consistency, g. | 1.8 | 1.8 |
| Time of setting, min. | 7.0 | 7.0 |
| Compressive strength, kg./sq.cm. | 1,050 | 1,040 |
| Film thickness, $\mu$ | 21 | 21 |
| Tensile strength, kg./sq.cm. | 99 | 99 |
| Solubility & Disintegration, % | 0.03 | 0.03 |

EXAMPLES 8 TO 10

Using 60 parts of acrylic acid, 40 parts of 3-butene-1,2,3-tricarboxylic acid and ammonium subsulfate in an amount of 2% with respect to the monomers, the procedure was repeated in the same manner as in Example 1 except that the amount of water and the period of time over which the polymerization was effected are changed as mentioned in Table 4 below and a chain transfer agent (for example, isopropyl alcohol — hereinafter referred to as IPA) was used in an amount as mentioned below. The resulting resin composition was observed to have about 30 percent of solid materials.

The resin composition was then concentrated to increase the concentration of the solid materials and the viscosity, thereby securing a higher compressive strength. With the change of the viscosity while keeping the solid concentration at 46 percent, the cement composition thus obtained was tested in the same manner as in Example 1. The materials used, conditions and results will be set forth in Table 4.

Table 4

| Examples | 8 | 9 | 10 |
|---|---|---|---|
| IPA, parts | 40 | 30 | 0 |
| Water, parts | 160 | 170 | 200 |
| Time of polymerization, hrs. | 7 | 8 | 9 |
| Solids of initial resin, % | 30 | 30 | 30 |
| Viscosity of initial resin, cps. | 500 | 800 | 1,000 |
| Viscosity of the concentrated resin, cps. | 1,600 | 2,800 | 3,600 |
| Standard consistency, g. | 1.9 | 1.8 | 1.6 |
| Time of setting, min. | 6.0 | 6.5 | 6.5 |
| Compressive strength, kg./sq.cm. | 910 | 950 | 1,100 |
| Film thickness, $\mu$ | 20 | 21 | 19 |
| Tensile strength, kg./sq.cm. | 50 | 60 | 68 |
| Solubility & Disintegration, % | 0.03 | 0.03 | 0.03 |

COMPARATIVE EXAMPLE

Using polycarboxylate cements commercially available, the procedures were repeated in the same manner as in Example 1 to give the following results:

Table 5

| Polycarboxylate cements | Sankin Carlon manufactured by Sankin Kagaku K. K., Japan | Carbolit manufactured by Jishi Kagaku K. K., Japan | Durelon manufactured Espe GmbH, W. Germany |
|---|---|---|---|
| Standard consistency, g. | 1.5 | 1.5 | 1.5 |
| Time of setting, minutes | 6.5 | 5.5 | 7.5 |
| Compressive strength, kg./sq.cm. | 630 | 630 | 560 |
| Film thickness, $\mu$ | 17 | 35 | 22 |
| Tensile strength, kg./sq.cm. | 45 | 70 | 94 |

What is claimed is:

1. A dental cement composition comprising:
   A. an aqueous solution of a resin prepared by copolymerizing:
      1. about 5 to 60 parts by weight of 3-butene-1,2,3-tricarboxylic acid,
      2. about 40 to 95 parts by weight of an $\alpha,\beta$-olefinically unsaturated monocarboxylic acid, and
      3. about 0 to 15 parts by weight of an additional polymerizable monomer,
   said copolymer having a molecular weight between about 5,000 and 250,000, said aqueous solution containing at least about 40% resin solids; and
   B. a metal oxide,
   C. the ratio of the copolymer to the metal oxide being about 1:1 to about 1:4.

2. A dental cement composition, as in claim 1 wherein the copolymer is formed by copolymerizing (A)(1) and (A)(2).

3. The dental cement composition of claim 1, wherein the $\alpha,\beta$-olefinically unsaturated monocarboxylic acid is selected from the group consisting of acrylic acid and methacrylic acid.

4. The dental cement composition of claim 1, wherein the additional polymerizable monomer is selected from the group consisting of esters of acrylic acid and methacrylic acid, an unsaturated carboxylic acid and esters thereof 3butene-1,2,3-tricarboxylic acid alkyl ester, vinyl acetate and styrene.

5. The dental cement composition of claim 1, wherein the aqueous copolymer solution has a solids concentration of about 40 to 60% and a viscosity of about 100 to 8,000 cps.

6. The dental cement composition of claim 1, wherein a metal oxide calcined at about 800° to 1300°C. is used.

7. The dental composition of claim 1, wherein the metal oxide is one or more members selected from the group consisting of oxides of zinc, magnesium, silicon, bismuth, barium, calcium, aluminum and titanium.

8. The dental composition of claim 1, containing metal halides, phosphates, sulfates, borates or silicates.

* * * * *

UNITED STATES PATENT OFFICE
CERTIFICATE OF CORRECTION

PATENT NO. : 3,962,267
DATED : June 8, 1976
INVENTOR(S) : Narishige Suzuki et al It is certified that error appears in the above–identified patent and that said Letters Patent are hereby corrected as shown below:

On the surface page of the Letters Patent, the assignee is referred to as Shofu Dental Corporation, and should be changed to --Shofu Dental Mfg. Co., Ltd.--

Signed and Sealed this

Seventh Day of September 1976

[SEAL]

Attest:

RUTH C. MASON
*Attesting Officer*

C. MARSHALL DANN
*Commissioner of Patents and Trademarks*